US006534626B1

(12) United States Patent
Oravecz et al.

(10) Patent No.: US 6,534,626 B1
(45) Date of Patent: Mar. 18, 2003

(54) CHEMOKINE VARIANTS

(75) Inventors: Tamas Oravecz, Palo Alto, CA (US); Michael A. Norcross, Bethesda, MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 09/555,663

(22) PCT Filed: Dec. 1, 1998

(86) PCT No.: PCT/US98/25492

§ 371 (c)(1),
(2), (4) Date: Sep. 14, 2000

(87) PCT Pub. No.: WO99/28474

PCT Pub. Date: Jun. 10, 1999

Related U.S. Application Data

(60) Provisional application No. 60/067,033, filed on Dec. 1, 1997.

(51) Int. Cl.[7] .......................... C07K 5/00; C12N 15/74; C12P 19/34; C07H 21/04
(52) U.S. Cl. ................... 530/300; 500/324; 435/320.1; 435/91.1; 536/23.1; 536/24.33
(58) Field of Search ........................ 424/185.1, 195.11, 424/198.1; 435/320.1, 7.1, 7.2, 69.1, 91.1; 436/501; 530/300, 324; 536/23.1, 24.3, 24.33

(56) References Cited

FOREIGN PATENT DOCUMENTS

| EP | 0 905 241 A | 3/1999 | ............ C12N/15/19 |
|---|---|---|---|
| WO | WO 94 09132 A | 4/1994 | ............ C12N/15/12 |
| WO | WO 94 29341 A | 12/1994 | ............ C07K/13/00 |
| WO | WO 96 40162 A | 12/1996 | ............ A61K/31/70 |
| WO | WO 97 44462 A | 11/1997 | ............ C12N/15/19 |
| WO | WO 97/44462 | * 11/1997 | |

OTHER PUBLICATIONS

Sequence alignment of SEQ ID No.: 1. Arenzana–Seisdedos et al. from WO 9744462–A. GenEmbl accession No.: A67989. Nov. 27, 1997.*
Sequence alignment of SEQ ID No.: 2. Arenzana–Seisdedos et al. from WO 9744462–A. Geneseq accession No.: AAW29538. Nov. 27, 1997.*
Mosier et al. 1999. Highly potent Rantes analogues either prevent CCR5–using human immunodeficiency virus type 1 infection in vivo and rapidly select for CXCR4–using variants. J Virol. 73(5): 3544–3550.*
Daar et al. 1990. High concentrations of recombinant soluble CD4 are required to neutralize primary human immunodeficiency virus type 1 isolates. PNAS 87: 6574–6578.*
Durum et al. 1993. Fundamental Immunology, third edition. Capter 21. "Proinflammatory cytokines and immunity", pp. 801–835.*
Arenzana–Seisdedos et al. 1996. HIV blocked by chemokine antagonist. Nature. vol. 383. p. 400.*
Proost P. et al. "Truncation of MDC chemokine by CD26/dipeptidyl peptidase IV beyond its predicted cleavage site affects chemotactic activity and CC chemokine receptor 4 interaction", *J . Bio. Chem.* 274(7):3988–3993, Feb. 12, 1999.
Schols D. et al. "CD36–processed Rantes (3–68), but not intact Rantes, has potent anti–HIV activity", *Antiviral Research* 39(3):175–187, Oct. 1998.
Proost P. et al. "Amino–terminal truncation of chemokines by CD26/dipeptidyl–peptidase IV", *J. Bio. Chem.* 273(13):7222–7227, Mar. 27, 1998.
Oravecz T. et al. "Regulation of the receptor specificity and function of the chemokine rantes (regulated on activation, normal T cell expressed and secreted) by dipeptidyl peptidase IV (CD26)—Mediated Cleavage", *J. Exp. Med.* 186(11):1865–1872, Dec. 1, 1997.
Arenzana–Seisdedos F. et al. "HIV blocked by chemokine antagonist", *Nature* 383(6599):400, Oct. 3, 1996.
Gong J. –H. et al. "Rantes and MCP–3 antagonists bind multiple chemokine receptors", *J. Bio. Chem.* 271(18):10521–10527, May 3, 1996.
Noso N. et al. "Identification on an N–terminally truncated form of the chemokine rantes and granulocyte–macrophage colony–stimulating factor, a major eosinophil attractants released by cytokine–stimulated dermal fibroblasts", *J. of Immunol.* 156(5):1946–1953, Jan. 1, 1996.
Oravecz T. et al. "Beta–chemokine inhibition of monocytotropic HIV–1 infection" *J. of Immunol.* 157:1329–1332, 1996.
Tanaka T. et al. "Enhancement of antigen–induced T–cell proliferation by soluble CD26/dipeptidyl peptidase IV", *Proc. Natl. Acad. Sci. USA* 91(1):3082–3086, Apr. 1, 1994.

* cited by examiner

*Primary Examiner*—James Housel
*Assistant Examiner*—Shanon Foley
(74) *Attorney, Agent, or Firm*—Needle & Rosenberg, PC

(57) ABSTRACT

The present invention provide the nucleotide and amino acid sequence of truncated RANTES (3–68) which has the same amino acid sequence as the wild-type RANTES, but with a serine/proline truncation at positions 1 and 2 from the N-terminus, respectively.

7 Claims, 8 Drawing Sheets

Figure 8

Nucleotide sequence of CD26 truncated RANTES chemokine (SEQ ID NO:1):

5'- TATTCCTCGGACACCACACCCTGCTGCTTTGCCTACATTGC-
CCGCCCACTGCCCCGTGCCCACATCAAGGAGTATT
TCTACACCAGTGGCAAGTGCTCCAACCCAGCAGTCGTCTTTGT
CACCCGAAAGAACCGCCAAGTGTGTGCCAACCCAGAGAAGAA
ATGGGTTCGGGAGTACATCAACTCTTTGGAGATGAGC -3'

Amino acid sequence of CD26 truncated RANTES chemokine (SEQ ID NO:2):

N- YSSDTTPCCFAYIARPLPRAHIKEYFYTSGKCSNPAVVFVTRK

SEQUENCE LISTING

```
<160> NUMBER OF SEQ ID NOS: 2

<210> SEQ ID NO 1
<211> LENGTH: 198
<212> TYPE: DNA
<213> ORGANISM: Homo sapiens
<220> FEATURE:
<221> NAME/KEY: CDS
<222> LOCATION: (1)..(198)

<400> SEQUENCE: 1 tat tcc tcg gac acc aca ccc tgc tgc ttt gcc tac att gcc cgc cca         48
Tyr Ser Ser Asp Thr Thr Pro Cys Cys Phe Ala Tyr Ile Ala Arg Pro
 1               5                  10                  15 ctg ccc cgt gcc cac atc aag gag tat ttc tac acc agt ggc aag tgc         96
Leu Pro Arg Ala His Ile Lys Glu Tyr Phe Tyr Thr Ser Gly Lys Cys
             20                  25                  30 tcc aac cca gca gtc gtc ttt gtc acc cga aag aac cgc caa gtg tgt        144
Ser Asn Pro Ala Val Val Phe Val Thr Arg Lys Asn Arg Gln Val Cys
```

-continued

```
                 35                  40                  45
gcc aac cca gag aag aaa tgg gtt cgg gag tac atc aac tct ttg gag    192
Ala Asn Pro Glu Lys Lys Trp Val Arg Glu Tyr Ile Asn Ser Leu Glu
        50                  55                  60 atg agc                                                            198
Met Ser
 65

<210> SEQ ID NO 2
<211> LENGTH: 66
<212> TYPE: PRT
<213> ORGANISM: Homo sapiens

<400> SEQUENCE: 2

Tyr Ser Ser Asp Thr Thr Pro Cys Cys Phe Ala Tyr Ile Ala Arg Pro
 1               5                  10                  15

Leu Pro Arg Ala His Ile Lys Glu Tyr Phe Tyr Thr Ser Gly Lys Cys
                20                  25                  30

Ser Asn Pro Ala Val Val Phe Val Thr Arg Lys Asn Arg Gln Val Cys
            35                  40                  45

Ala Asn Pro Glu Lys Lys Trp Val Arg Glu Tyr Ile Asn Ser Leu Glu
        50                  55                  60

Met Ser
 65
```

US 6,534,626 B1

CHEMOKINE VARIANTS

This is a 371 national phase application filed from and claims priority to international patent application no. PCT/US98/25492, filed Dec. 1, 1998, which claims priority from provisional patent application, U.S. Ser. No. 60/067,033 filed Dec. 1, 1997 which is hereby incorporated by reference in its entirety.

FIELD OF THE INVENTION

The present invention relates generally to chemoattractant cytokines, called chemokines, and more specifically to truncated or variant forms of chemokines which have functions different from their wild-type counterparts, methods of use and methods of producing such variant chemokines.

BACKGROUND OF THE INVENTION

Immunomodulatory proteins include chemotactic cytokines, called "chemokines". Chemokines are small molecular weight immune ligands which are chemoattractants for leukocytes, such as especially neutrophils, basophils, monocytes and T cells. There are two major classes of chemokines which both contain four conserved cysteine residues which form disulfide bonds in the tertiary structure of the proteins. The α class is designated C-X-C (where X is any amilno acid), which includes IL-8, CTAP-III, gro/MGSA and ENA-78; and the β class, designated C-C, which includes MCP-1, MIP-1α and β, and regulated on activation, normal T expressed and secreted protein (RANTES). The designations of the classes are according to whether an intervening residue spaces the first two cysteines in the motif. In general, most C-X-C chemokines are chemoattractants for neutrophils but not monocytes, whereas C-C chemokines appear to attract monocytes but not neutrophils. Recently, a third group of chemokines, the "C" group, was designated by the discovery of a new protein called lymphotactin (Kelner, et al., Science, 266:1395–1933, 1994). The chemokine family is believed to be critically important in the infiltration of lymphocytes and monocytes into sites of inflammation.

Monocytes differentiate into macrophages as they migrate from the blood to tissues during immune surveillance. At sites of inflammation, monocyte infiltration and macrophage accumulation are coordinated, in part, by chemokines (1). The mechanisms that control the recruitment of monocytes and macrophages by chemoattractants have not been clearly defined, but they may include regulation of the expression of chemokines and their receptors (2) as well as the modification of chemokine activity by posttranslational processing (3–5). Several chemokines share a conserved NH2-X-Pro sequence (X, any amino acid) at the NH2-terminus (6), which conforms to the substrate specificity of dipeptidyl exopeptidase IV (DPPIV) (7). DPPIV cleaves the first two amino acids from peptides with penultimate proline or alanine residues, although no natural substrate with immune function has been identified. This enzyme is also a leukocyte differentiation antigen, known as CD26 (8–10), that is expressed on the cell surface mostly by T lymphocytes and macrophages. Expression of CD26 has been associated with T cell activation (8–10) and with susceptibility of a T cell line to infection with macrophage-tropic (M-tropic) HIV-1 (11).

SUMMARY OF THE INVENTION

The present invention is based on the discovery that chemokines having a particular N-terminal motif are natural substrates for a dipeptidyl dipeptidase (DPPIV). Prior to the present invention, it was known that CD26 is a leukocyte activation marker that possesses dipeptidyl peptidase IV (DPPIV) activity but natural substrates had not been identified. The present invention shows that several chemokines, including RANTES (regulated on activation, normal T expressed and secreted) are substrates for recombinant soluble human CD26 (sCD26). The present invention shows that DPPIV, e.g., CD26-mediated processing, together with cell activation induces changes in receptor expression and provides a mechanism for differential cell recruitment and for the regulation of target cell specificity of chemokines.

Abbreviations: [Ca2+]i, cytosolic free Ca2+ concentration; DPPIV, dipeptidyl peptidase IV; ES-MS, electrospray mass spectromety; M-tropic, macrophage-tropic; pNA, p-nitroanilide; rh, recombinant human; sCD26, soluble CD26.

In a first embodiment, the invention provides the nucleotide and amino acid sequence of truncated RANTES (3–68), which is the same as the wild-type RANTES with a Serine/Proline truncation at positions 1 and 2 from the N-terminus, respectively.

In another embodiment, the invention provides a method for identifying a compound which modulates dipeptidyl peptidase IV (DPPIV)-mediated chemokine processing. The method includes a) incubating components comprising the compound, DPPIV and a chemokine under conditions sufficient to allow the components to interact; and b) determining the N-terminal amino acid sequence of the chemokine before and after incubating in the presence of the compound. Modulation of DPPIV-mediated chemokine processing may be inhibition or stimulation of processing, for example. Compounds which modulate such processing include peptides, peptidomimetics, and other small molecule compounds.

In another embodiment, the invention provides a method of inhibiting membrane fusion between HIV and a target cell or between an HIV-infected cell and a CD4 positive uninfected cell by contacting the target or CD4 positive cell with a fusion-inhibiting effective amount of the polypeptide of SEQ ID NO:2 (RANTES 3–68).

The invention also provides a method of treating a subject having or at risk of having an HIV infection or disorder, including administering to the subject, a therapeutically effective amount of a polypeptide of SEQ ID NO:2, wherein the polypeptide inhibits cell-cell fusion in cells infected with HIV The invention also provides a method of treating a subject having an HIV-related disorder associated with expression of CCR5 comprising administering to an HIV infected or susceptible cell of the subject, a polypeptide of SEQ ID NO:2 or a nucleic acid sequence encoding the polypeptide of SEQ ID NO:2 or other variant chemokine. Preferably, the subject is a human.

Also included are pharmaceutical compositions including the polypeptide of SEQ ID NO:2 or CD26, in pharmaceutically acceptable carriers.

In yet another embodiment, the invention provides a method for producing a variant chemokine having an activity different from the activity of the wild-type chemokine, including contacting the wild-type chemokine with an N-terminal processing effective amount of dipeptidyl peptidase IV (DPPIV), thereby truncating the chemokine and producing a variant chemokine. Chemokines may include, but are not limited to, RANTES, MIP-1, IP-10, eotaxin, MDC, and MCP-2.

The invention also provides a method for inhibiting HIV-1 replication in a host cell susceptible to HIV-1 infection, comprising contacting the cell or the host with an effective amount of dipeptidyl peptidase IV (DPPIV) enzyme such that macrophage-derived chemokine (MDC) is cleaved to produce truncated MDC, thereby providing antiviral activity and inhibiting HIV-1 replication and a A method for inhibiting HIV-1 replication in a host cell susceptible to HIV-1 infection, comprising contacting the cell or the host with an effective amount of dipeptidyl peptidase IV (DPPIV) enzyme such that RANTES is cleaved to produce truncated RANTES, thereby providing antiviral activity and inhibiting HIV-1 replication.

In another embodiment, the invention provides a method for inhibiting dipeptidyl peptidase IV (DPPIV)-mediated chemokine processing comprising contacting DPPIV with an inhibiting effective amount of a compound which inhibits DPPIV expression or activity.

In another embodiment, the invention provides a method for inhibiting an allergic or inflammatory reaction in a subject, comprising administering to the subject an effective amount of Dipeptidyl peptidase IV (DPPIV) enzyme such that a chemokine is cleaved to produce a truncated chemokine, thereby inhibiting an allergic or inflammatory reaction. Preferably, the chemokine is eotaxin.

In another embodiment, the invention provides a method for accelerating angiogenesis or wound healing in a subject, comprising administering to the subject an effective amount of an inhibitor of dipeptidyl peptidase IV (DPPIV) enzyme activity or gene expression or a DPPIV-insensitive chemokine, such that chemolcine processing is inhibited, thereby accelerating angiogenesis or wound healing. One exemplary chemokine useful in the method for accelerating angiogenesis is IP-10.

In all of the above methods, the exemplary DPPIV shown in the present invention is CD26.

In yet another embodiment, the invention provides a method for diagnosis or prognosis of a subject having a chemokine-associated disorder. The method includes identifying the presence of a chemokine of interest from a specimen isolated from the subject; determining the amino-terminal sequence of the chemokine, wherein a full-length amino acid sequence is indicative of the presence of a wild-type chemokine polypeptide and a truncated amino-terminal sequence is indicative of the presence of a variant chemokine; and determining the concentration of wild-type chemokine as compared to variant chemokine, thereby providing a diagnosis of the subject.

BRIEF DESCRIPTION OF THE DRAWINGS

FIG. 8. The nucleotide and deduced amino acid sequences for RANTES 3–68 (SEQ ID NO:1 and 2, respectively) are shown.

DESCRIPTION OF THE PREFERRED EMBODIMENTS

Figure 1:
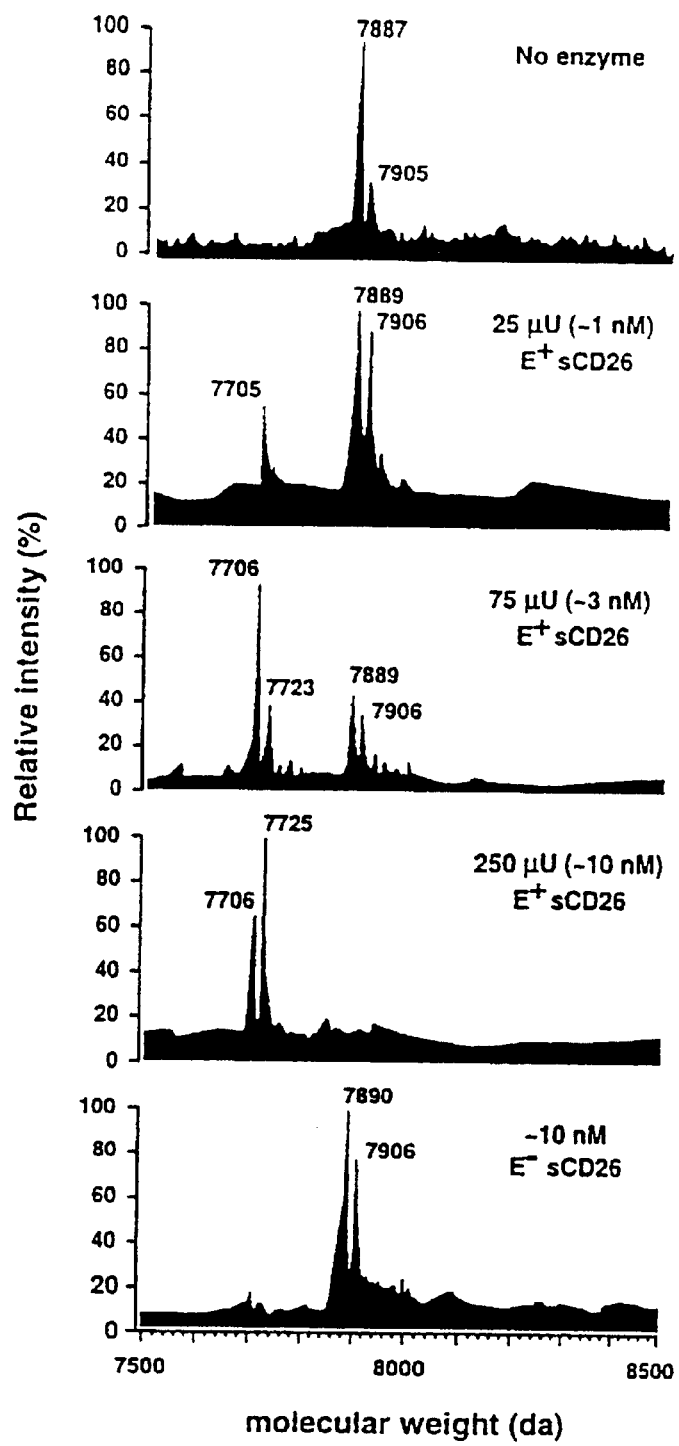
FIG. 1. RANTES cleavage products after digestion with sCD26. RANTES was incubated overnight with the indicated amounts of enzymatically active (E+) or enzymatically deficient (E( ) sCD26 and samples were subjected to ES-MS analysis. The peaks in the spectrum at masses of 7905 to 7906 and 7887 to 7890 are tentatively identified as [M+K+]+ of RANTES with (7904 daltons) and without (7886 daltons) a molecule of H2O, respectively; the labeled peaks at the left of the spectrum correspond to each of these molecular ions minus a Ser-Pro dipeptide (184 daltons).

The present invention is based on the discovery of variant forms of chemokines which have different functions than their wild-type counterparts. These variant chemokines are produced by cleavage with a dipeptidyl peptidase IV (DPPIV) which cleaves at the N-terminus of a polypeptide when there is a proline or an alanine at position 2.

Overview

CD26 is a leukocyte activation marker that possesses dipeptidyl peptidase IV (DPPIV) activity but whose natural substrates and immunological functions have not been clearly defined. Several chemokines, including RANTES (regulated on activation, normal T expressed and secreted) have now been shown to be substrates for recombinant soluble human CD26 (sCD26). The truncated RANTES (3–68) lacked the ability of native RANTES(1–68) to increase the cytosolic calcium concentration in human monocytes, but it still induced this response in macrophages activated with macrophage colony-stimulating factor (M-CSF). Analysis of chemokine receptor messenger RNAs and patterns of desensitization of chemokine responses showed that the differential activity of the truncated molecule results from an altered receptor specificity. RANTES (3–68) showed a reduced activity, relative to that of RANTES(1–68), with cells expressing the recombinant CCR1 chemokine receptor, but it retained the ability to stimulate CCR5 receptors and to inhibit the cytopathic effects of HIV-1. Our results indicate that CD26-mediated processing together with cell activation induced changes in receptor expression provide an integrated mechanism for differential cell recruitment and for the regulation of target cell specificity of RANTES, and possibly other chemokines.

Nucleotide and Amino Acid Sequences of RANTES Variant (3–68) or Other Chemokine Variants In a first embodiment, the invention provides a substantially purified RANTES variant polypeptide exemplified by the amino acid sequence of SEQ ID NO:2. The term "polypeptide" means any chain of amino acids, regardless of length or post-translational modification (e.g., glycosylation or phosphorylation), and includes natural proteins as well as synthetic or recombinant polypeptides and peptides.

The term "substantially pure" as used herein refers to RANTES (3–68) or other variant chemokine which is substantially free of other proteins, lipids, carbohydrates or other materials with which it is naturally associated. One skilled in the art can purify RANTES (3–68) or other variant chemokine using standard techniques for protein purification. The substantially pure polypeptide will yield a single major band on a non-reducing polyacrylamide gel. The purity of the RANTES (3–68) or other variant chemokine polypeptide can also be determined by amino-terminal amino acid sequence analysis. RANTES (3–68) or other variant chemoline polypeptide includes functional fragments of the polypeptide, as long as the activity of RANTES (3–68) or other variant chemokine remains. Such functional variants would include the N-terminus which is truncated as compared to the wild-type RANTES or other chemokine. The term "variant" as used herein refers to a polypeptide having substantially the same polypeptide sequence as the corresponding wild-type polypeptide, with minor amino acid variations. These amino acid variations result in a polypeptide having various additional and/or different functions from the wild-type polypeptide, and possibly having altered receptor specificity as compared to the wild-type polypeptide. Smaller peptides containing the biological activity of RANTES (3–68) or other variant chemokine are included in the invention. The term "substantially pure," when referring to an chemokine polypeptide, means a polypeptide that is at least 60%, by weight, free from the proteins and naturally-occurring organic molecules with which it is naturally associated. A substantially pure RANTES (3–68) or other variant chemokine polypeptide is at least 75%, more preferably at least 90%, and most preferably at least 99%, by weight, RANTES (3–68) or other variant chemokine polypeptide. A substantially pure RANTES (3–68) or other variant chemokine can be obtained, for example, by extraction from a natural source; by expression of a recombinant nucleic acid encoding a RANTES (3–68) or other variant chemokine polypeptide, or by chemically synthesizing the protein. Purity can be measured by any appropriate method, e.g., column chromatography, polyacrylamide gel electrophoresis, or HPLC analysis.

Minor modifications of the recombinant RANTES (3–68) or other variant chemokine primary amino acid sequence may result in proteins which have substantially equivalent activity as compared to the RANTES (3–68) or other variant chemokine polypeptide described herein. Such modifications may be deliberate, as by site-directed mutagenesis, or may be spontaneous. All of the polypeptides produced by these modifications are included herein as long as the biological activity of RANTES (3–68) or other variant chemokine still exists. Further, deletion of one or more amino acids can also result in a modification of the structure of the resultant molecule without significantly altering its biological activity. This can lead to the development of a smaller active molecule which would have broader utility.

The polynucleotide sequence encoding the RANTES (3–68) or other variant chemokine polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention provides isolated polynucleotides encoding the RANTES (3–68) or other variant chemokine polypeptide. In one embodiment, the polynucleotide is the nucleotide sequence of SEQ ID NO:1. These polynucleotides include DNA, cDNA and RNA sequences which encode RANTES (3–68) or other variant chemokine. It is understood that all polynucleotides encoding all or a portion of RANTES (3–68) or other variant chemokine are also included herein, as long as they encode a polypeptide with RANTES (3–68) or other variant chemokine activity (e.g., does not bind to CCR1 but binds to CCR5). Such polynucleotides include naturally occurring, synthetic, and intentionally manipulated polynucleotides. For example, RANTES (3–68) or other variant chemokine polynucleotide may be subjected to site-directed mutagenesis. The polynucleotide sequence for RANTES (3–68) or other variant chemokine also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of RANTES (3–68) or other variant chemokine polypeptide encoded by the nucleotide sequence is functionally unchanged. Abbreviations for the amino acid residues are follows: A, Ala; C, Cys; D, Asp: E, Glu: F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

As used herein, "polynucleotide" also refers to a nucleic acid sequence of deoxyribonucleotides or ribonucleotides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit.

An isolated polynucleotide as described herein is a nucleic acid molecule that is separated in some way from sequences in the naturally occurring genome of an organism. Thus, the term "isolated polynucleotide" includes any nucleic acid molecules that are not naturally occurring. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

Specifically disclosed herein is a DNA sequence containing the RANTES polypeptide gene encoding RANTES truncated at positions 1 and 2. The polynucleotide encoding RANTES (3–68) includes FIG. 8 (SEQ ID NO:1), as well as nucleic acid sequences complementary to SEQ ID NO:1. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO: 2 under physiological conditions or a close family member of RANTES. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the RANTES (3–68) or other variant chemokine polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981; Maniatis, et al., *Molecular Cloning: A Laboratory Manual,* Cold Spring Harbor, N.Y 1989).

The development of specific DNA sequences encoding RANTES (3–68) or other variant chemokine can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for RANTES (3–68) or other variant chemokine peptides having at least one epitope, using antibodies specific for RANTES (3–68) or other variant chemokine. Such antibodies can be either polyclonally or monoclonally derived and used to detect expression product indicative of the presence of RANTES (3–68) or other variant chemokine cDNA.

The isolated polynucleotide sequences of the invention also include sequences complementary to the polynucleotides encoding RANTES (3–68) or other variant chemokine (antisense sequences). Antisense nucleic acids are DNA or RNA molecules that are complementary to at least a portion of a specific mRNA molecule (Weintraub et al., Scientific American 262:40, 1990). The invention includes all antisense polynucleotides that inhibit production of RANTES (3–68) or other variant chemokine polypeptides. In the cell, the antisense nucleic acids hybridize to the corresponding mRNA, forming a double-stranded molecule. Antisense oligomers of about 15 nucleotides are preferred, since they are easily synthesized and introduced into a target RANTES (3–68) or other variant chemokine-producing cell. The use of antisense methods to inhibit the translation of genes is known in the art, and is described, e.g., in Marcus-Sakura (Anal. Biochem., 172:289, 1988).

In addition, ribozyme nucleotide sequences for RANTES (3–68) or other variant chemokine are included in the invention. Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes, tetrahymena-type (Hasselhoff (1988) Nature 334:585) and "hammerhead"-type. Tetrahymena-type ribozymes recognize sequences which are four bases in length, while "hammerhead"-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating a specific mRNA species, and 18-base recognition sequences are preferable to shorter recognition sequences.

DNA sequences encoding RANTES (3–68) or other variant chemokine can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the RANTES (3–68) or other variant chemokine polynucleotide sequences may be inserted into a recombinant expression vector. The term "recombinant expression vector" refers to a plasmid, virus or other vehicle known in the art that has been manipulated by insertion or incorporation of the RANTES (3–68) or other variant chemokine genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, m etallothionein I, or polyhedrin promoters).

Polynucleotide sequences encoding RANTES (3–68) or other variant chemokine can be expressed in either prokaryote or eukaryotes. Hosts can include microbial, yeast, insect and mammalian organisms. Methods of expressing DNA sequences having eukaryotic or viral sequences in prokaryote are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the RANTES (3–68) or other variant chemokine of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

Antibodies That Distinguish Wild-type Chemokine from Truncated Chemokine

The present invention also provides antibodies useful for distinguishing between wild-type and DPPIV-truncated chemokine polypeptides. Preferably, the antibodies are produced by using N-terminal peptides having about 8 or more amino acids. Therefore, antibodies produced will distinguish between a chemokine, such as RANTES, that contains N-terminal amino acids, and a chemokine that has been cleaved, for example by CD26. The preparation of polyclonal antibodies is well-known to those skilled in the art. See, for example, Green et al., *Production of Polyclonal Antisera*, in IMMUNOCHEMICAL PROTOCOLS (Manson, ed.), pages 1–5 (Humana Press 1992); Coligan et al., *Production of Polyclonal Antisera in Rabbits, Rats, Mice and Hamsters*, in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, Nature 256:495 (1975); Coligan et al., sections 2.5.1–2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., Purification of Immunoglobulin G (IgG), in METHODS IN MOLECULAR BIOLOGY, VOL. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., Int. J. Cancer 46:310 (1990), which are hereby incorporated by reference.

Alternatively, a therapeutically useful anti-RANTES (3–68) or other variant chemokine antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989), which is hereby incorporated in its entirety by reference. Techniques for producing humanized monoclonal antibodies are described, for example, by Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993), which are hereby incorporated by reference.

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994); Lonberg et al., Nature 368:856 (1994); and Taylor et al., Int. Immunol. 6:579 (1994), which are hereby incorporated by reference.

Antibody fragments of the present invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., Arch. Biochem. Biophys. 89:230 (1960); Porter, Biochem. J. 73:119 (1959); Edelman et al., METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., *Science* 242:423–426 (1988); Ladner et al., U.S. Pat. No. 4,946,778; Pack et al., *Bio/Technology* 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Lanick et al., METHODS: A COMPANION TO METHODS IN ENZYMOLOGY, VOL. 2, page 106 (1991).

Screen for Compounds Which Modulate DDPPIV

In another embodiment, the invention provides a method for identifying a compound which modulates dipeptidyl peptidase IV (DPPIV)-mediated chemokine processing. The method includes: a) incubating components comprising the compound, DPPIV and a chemokine under conditions sufficient to allow the components to interact; and b) determining the N-terminal amino acid sequence of the chemokine before and after incubating in the presence of the compound. Compounds that inhibit DPPIV include peptides, peptidomimetics, polypeptides, chemical compounds and biologic agents. Preferably the DPPIV is CD26. If a compound inhibits the DPPIV or CD26 enzymatic activity, the chemokine will have an N-terminal amino acid sequence which corresponds to the wild-type polypeptide. Alternatively, if the compound stimulates DPPIV or CD26 enzymatic activity, the chemokine will have a truncated amino-terminal amino acid sequence. The amino acid sequence can be determined by standard N-terminal sequencing methods or by contacting the chemokine with a monoclonal antibody which distinguishes between wild-type and truncated or variant chemokine, for example.

Incubating includes conditions which allow contact between the test compound and the chemokine and a DPPIV. Contacting includes in solution and in solid phase, or in a cell. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Methods for Producing Variant Chemokines

In another embodiment, the invention provides a method for producing a variant chemokine having an activity different from the activity of the wild-type chemokine, including contacting the wild-type chemokine with an N-terminal processing effective amount of dipeptidyl peptidase IV (DPPIV), thereby truncating the chemokine and producing a variant chemokine. The term "N-terminal processing effective amount" refers to that amount of a DPPIV that cleaves the amino terminus of a wild-type chemokine polypeptide to produce a chemokine lacking the first two amino terminal amino acids. For example, incubation of RANTES with an "N-terminal processing effective amount" of CD26 results in RANTES (3–68) which has different activity than wild type RANTES. Chemokines that contain amino acid motifs at the N-terminus include but are not limited to RANTES, MIP-1, IP-10, eotaxin, macrophage-derived chemokine (MDC) and MCP-2. Other chemokines known in the art can be assessed for sensitivity to cleavage by DPPIVs as described herein by determining the first two amino terminal amino acids.

Contacting the chemokine can be in vitro or in vivo. For example, a specimen isolated from a subject, such as a human, or a mixture or pure sample of chemokine, can be contacted with DPPIV in vitro. The contacting of the DPPIV and chemokine is deemed sufficient when cleavage of the chemokine has occurred. It may be desirable to only cleave a fraction of the total chemokine population, therefore, samples can be analyzed at various time of incubation to determine the optimal conditions for the desired concentration of wild-type versus truncated variant chemokine achieved.

The preferred chemokine illustrated herein is RANTES and the preferred DPPIV is CD26. Other chemokines and DPPIVs are also included in the method of the invention.

Inhibition of DPPIV

In another embodiment, the invention provides a method for inhibiting dipeptidyl peptidase IV (DPPIV)-mediated chemokine processing comprising contacting DPPIV with an inhibiting effective amount of a compound which inhibits DPPIV expression or activity. For example, the method includes inhibiting CD26 expression or activity. To determine whether the DPPIV activity or expression is inhibited, an assay to detect cleavage of a chemokine having an alanine or proline at position 2, or a Northern blot analysis, can be performed, respectively. Other standard methods can be used to detect inhition of gene expression or enzymatic activity. For example, incubation of CD26, RANTES and a compound suspected of inhibiting CD26 activity, would result in wild-type RANTES, but little or no cleaved RANTES (or RANTES "variant").

Methods of Use for Inhibiting HIV-1 Replication, Allergic or Inflammatory Reactions, and Angiogenesis In another embodiment, the invention provides a method for inhibiting HIV-1 replication in a host cell susceptible to HIV-1 infection, comprising contacting the cell or the host with an effective amount of dipeptidyl peptidase IV (DPPIV) enzyme such that macrophage-derived chemokine (MDC) or RANTES is cleaved to produce truncated MDC or RANTES, respectively, thereby providing antiviral activity and inhibiting HIV-1 replication. The present invention provides data demonstrating that cleaved RANTES blocks HIV-1 infection (EXAMPLE 7). While not wanting to be bound to a particular theory, it is believed that the activity of MDC is increased upon cleavage. MDC suppresses HIV-1 replication, thus, it is desirable for AIDS patients, or individuals at risk of HIV-1 infection to have increased levels of cleaved MDC. Other chemokines may also be useful in the method of the invention fro inhibiting HIV-1 replication.

In yet another embodiment, the invention provides a method for inhibiting an allergic or inflammatory reaction in a subject, comprising administering to the subject an effective amount of dipeptidyl peptidase IV (DPPIV) enzyme such that a chemokine is cleaved to produce a truncated chemokine, thereby inhibiting an allergic or inflammatory reaction. Preferably, a chemokine useful for inhibition allergic or inflammatory reactions is a truncated eotaxin.

The use of a truncated chemokine in the method of the invention may inhibit or depress an immune or inflammatory response where desirable, such as in graft rejection responses after organ and tissue transplantations, or autoimmune disease. Some of the commonly performed transplantation surgery today includes organs and tissues such as kidneys, hearts, livers, skin, pancreatic islets and bone marrow. However, in situations where the donors and recipients are not genetically identical, graft rejections can still occur. Autoimmune disorders refer to a group of diseases that are caused by reactions of the immune system to self antigens leading to tissue destruction. These responses may be mediated by antibodies, auto-reactive T cells or both. Some important autoimmune diseases include diabetes, autoimmune thyroiditis, multiple sclerosis, rheumatoid arthritis, systemic lupus erythematosis, and myasthenia gravis. Other allergic or inflammatory responses are included in the method of the invention.

In another embodiment, the invention provides a method for accelerating angiogenesis or wound healing in a subject, comprising administering to the subject an effective amount of an inhibitor of dipeptidyl peptidase IV (DPPIV) enzyme activity or gene expression or a DPPIV-insensitive chemokine, such that chemokine processing is inhibited, thereby accelerating angiogenesis or wound healing. For example, new blood vessels are required for tissue repair and enhanced blood vessel growth may aid in improving circulation to ischemic limbs and heart tissue suffering from atherosclerotic disease, healing skin ulcers or other wounds, and establishing tissue grafts. Preferably, a chemokine useful for accelerating angiogenesis is a wild-type IP-10. Cleavage of IP-10 appears to inactivate the activity of IP-10, therefore it is desirable to inhibit cleavage of IP-10. Alternatively, it may be desirable to provide a variant IP-10 polypeptide which contains an amino acid substitution at position 2, such that neither proline nor alanine is present, which would result in a DPPIV-insensitive chemokine. However, such a variant must retain the activity of wild-type IP-10, e.g., a chemoattractant for NK cells.

Methods of Diagnosis of Chemokine-associated Disorders

In another embodiment, the invention provides a method for diagnosis and prognosis of chemokine-associated disorders. The method includes identifying the presence of a chemokine of interest from a specimen isolated from the subject; determining the amino-terminal sequence of the chemokine, wherein a full-length amino acid sequence is indicative of the presence of a wild-type chemokine polypeptide and a truncated amino-terminal sequence is indicative of the presence of a variant chemokine; and determining the concentration of wild-type chemokine as compared to variant chemokine, thereby providing a diagnosis of the subject. This method is also useful for prognosis of a subject, for example, a subject having AIDS and being treated with a particular therapeutic regimen. The amino-terminal sequence of the chemokine is determined, for example, by standard N-terminal sequencing, or by contacting the chemokine with an antibody which distinguishes wild-type from variant chemokine polypeptide, as described above. Use of monoclonal antibodies, for example, allows simple detection by ELISA or other methods. Specimens useful for such diagnosis include but are not limited to blood, sputum, urine, saliva, cerebrospinal fluid, and serum.

Pharmaceutical Compositions

The invention also includes various pharmaceutical compositions that are useful for therapeutic applications as described herein. The pharmaceutical compositions according to the invention are prepared by bringing a polypeptide such as SEQ ID NO:2 (RANTES (3–68)) or a DPPIV, such as CD26, into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 15th ed. Easton: Mack Publishing Co., 1405–1412, 1461–1487 (1975) and *The National Formulary XIV.,* 14th ed. Washington: American Pharmaceutical Association (1975), the contents of which are hereby incorporated by reference. The pH and exact concentration of the various components of the pharmaceutical composition are adjusted according to routine skills in the art. See *Goodman and Gilman's The Pharmacological Basis for Therapeutics* (7th ed.).

In another embodiment, the invention relates to a method of treating a subject having an HIV-related disorder associated with expression of CCR5 including administering to an HIV-infected or susceptible cell of a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human. Such a method can be performed in vivo or ex vivo for example. For example, a vector containing a nucleic acid sequence encoding SEQ ID NO:2 or another truncated chemokine can be utilized for introducing the composition into a cell of the subject.

In another embodiment, the invention provides a method of treating a subject having or at risk of having an HIV infection or disorder, comprising administering to the subject, a therapeutically effective amount of a polypeptide of SEQ ID NO:2, wherein the polypeptide inhibits cell-cell fusion in cells infected with HIV. This method is performed as discussed above.

In another embodiment, the invention provides a method of inhibiting membrane fusion between HIV and a target cell or between an HIV-infected cell and a CD4 positive uninfected cell comprising contacting the target or CD4 positive cell with a fusion-inhibiting effective amount of the polypeptide of SEQ ID NO:2.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science*, 249: 1527–1533 (1990), which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al. (eds.) (1990) GOODMAN AND GILMAN'S: THE PHARMACOLOGICAL BASES OF THERAPEUTICS, 8th ed., Pergamon Press; and REMINGTON'S PHARMACEUTICAL SCIENCES, 17th ed. (1 990), Mack Publishing Co., Easton, Pa., each of which is herein incorporated by reference.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Materials and Methods

Cell cultures and transfections. Monocytes were isolated from human PBMCs of healthy donors by counter-current centrifugal elutriation Monocyte-derived macrophages were prepared by culturing monocytes for 6 days at a density of 106 cells/ml in serum-free macrophage medium (Gibco BRL, Grand Island, N.Y.) supplemented with recombinant human (rh) M-CSF (10 ng/ml) (R&D Systems, Minneapolis, Minn.).

Human embryonic kidney (HEK)-293 cells grown to confluence in DMEM supplemented with 10% heat-inactivated FCS, penicillin, streptomycin, 2 mM glutamine, and 10 mM Hepes (pH 7.4) were transfected with plasmid DNA encoding CCR5 (12). CD4-positive human osteosarcoma (HOS-CD4) cell lines transfected with individual chemokine receptor cDNAs were obtained from N. Landau, and were grown in the above culture medium supplemented with puromycin.

The derivative of the PM1 cell line chronically infected with the recombinant HIV-1 clone MV3-HXB2 has been described previously (11). sCD26 cleavage and electrospray mass spectrometry (ES-MS). To create the recombinant soluble human CD26 (sCD26) construct, a signal peptidase cleavage consensus sequence was introduced in the pTZ-CD26.11 cDNA (13) by a Leu to Ala substitution at residue 28. To obtain enzyme negative construct, the Ser at residue 630 was further replaced by Ala. The two constructs were cloned into the pEE14.HCMV expression vector and transfected into CHO-K1 cells (14). The enzymatically active (E+) and enzymatically deficient (E−) sCD26 proteins were purified from cell culture supernatants of stable transfectants, and were tested in Western blotting and DPPIV enzyme assays (15). Both proteins had a relative molecular weight of 110 kDa, bound equally well to several CD26 mAbs, but only the E+ sCD26 showed detectable DPPIV activity. rhRANTES, MCP-1, MCP-2, eotaxin, and IP-10 (100 nM) (Peprotech, Rocky Hill, N.J.) were incubated overnight at 37° C. with different amounts of E+ or E(sCD26 in 50 (l of PBS. Samples were desalted and concentrated by using a peptide Wap (Michrom BioResources, Inc., Auburn, Calif.), or a reversed-phase (RP) HPLC interface. ES-MS analysis of samples was performed in 50% acetonitrile, supplemented with 0.1% (v/v) glacial acetic acid, using a Finnigan (San Jose, Calif.) TSQ 7000 triple-stage quadrupole mass spectrometer. Several scans were summed to obtain the final spectrum. Peptide synthesis. Full-length and truncated RANTES were synthesized with an Applied Biosystems (Foster City, Calif.) peptide synthesizer according to fluorenyl methoxycarbonyl (FMOC) chemistry. FMOC-protected amino acids were added stepwise with ninhydrin monitoring at each cycle. The peptides were folded by air oxidation and purified by RP HPLC. Peptide sequences were confirmed by amino acid analysis and Edman sequence analysis, and the molecular masses were confirmed by ES-MS analysis. There was no substantial difference in the activities of chemically synthesized full-length RANTES and rhRANTES(1–68) as judged by the $Ca^{2+}$ influx and anti-HIV-1 assays used in this study.

Colorimetric DPPIV Enzyme Assay

The p-nitroanilide (pNA)-conjugated Gly-Pro dipeptide substrate and test competitors were mixed and added to human placental DPPIV (Enzyme System Products), and the resulting mixture was incubated at room temperature in a final volume of 150 (1 containing 50 mM tris-HCl (pH 8.0) and 0.15 M NaCl. The final concentrations of DPPIV and Gly-Pro-pNA were 1.25 mU/ml and 400 (M, respectively. The kinetics of the enzyme reaction were monitored by measuring absorbance at 405 nm with a Vmax kinetic microplate reader (Molecular Devices, Menlo Park Calif.). The percentage inhibition of enzyme activity was calculated from the maximal velocity for each sample and from that apparent in the absence of competitor (100% activity).

RT-PCR analysis. Isolated total cellular RNA of monocytes was subjected to first-strand cDNA synthesis. PCR amplification of cDNA was performed for 30 cycles (92° C. for 1 min, 40° C. for 1 min, 72° C. for 1 min) with primers specific for CCR1, CCR2b, CCR3, CCR5, CXCR4, and GAPDH. Separated products were stained with SYBR Green I (Molecular Probes, Eugene, Oreg.).

Cytosolic Calcium Measurements

Cells (107/ml) were washed and incubated in the dark at 37° C. for 45 min in $Ca^{2+}$ buffer [136 mM NaCl, 4.8 mM KCl, 5 mM glucose, 1 mM CaCl2, 20 mM Hepes (pH 7.4)] supplemented with 5 (M Fura-2 acetoxymethyl ester that had been premixed with 10% Pluronic<< F-127 (Molecular Probes). The cells were then washed and resuspended at 2 (106 cells/ml in $Ca^{2+}$ buffer containing BSA (1 mg/ml), and portions (2 ml) of the cell suspension were exposed at different time points in a stirred cuvette at 37° C. to chemokines. Fluorescence was monitored with a Photon Technology International d scan (South Brunswick, N.J.), and data were recorded as the relative ratio of fluorescence at excitation wavelengths of 340 and 380 nm, with emission measured at 510 nm. After each measurement, maximal and minimal fluorescence were assessed by addition of 20 (M ionomycin followed by 5 mM MnCl2. Assay for HIV-1-induced cytopathicity. HOS-CD4.CCR5 cells (2 (104) were incubated for 1 hour at 37° C. with RANTES variants in 150 (1 of culture medium containing 20% FCS, and were then mixed with 50 (1 (2 (105 cells/ml) of uninfected PM1 cells or PM1 cells chronically infected with MV3-HXB2 virus. After 3 days, photomicrographs of cultures were taken and cell viability was measured by adding of 50 (1 of 1 mg/ml 2,3-bis[2-methoxy-4-nitro-5-sulfophenyl]-2H-tetrazolium-5-carboxanilide solution containing 20 (M phenazine methosulfate and recording the OD at 450 nm. Data are expressed as the percentage inhibition of cytopathicity [calculated as 100% ((R (V)/(U (V), where U, V, and R represent OD values obtained for HOS-CD4.CCR5 cells cultured with uninfected PM1 cells, or with HIV-1-infected cells in the absence or presence of chemokine, respectively].

EXAMPLE 2

RANTES, MCP-2, Eotaxin, and IP-10 Are Substrates of CD26

Figure 2:
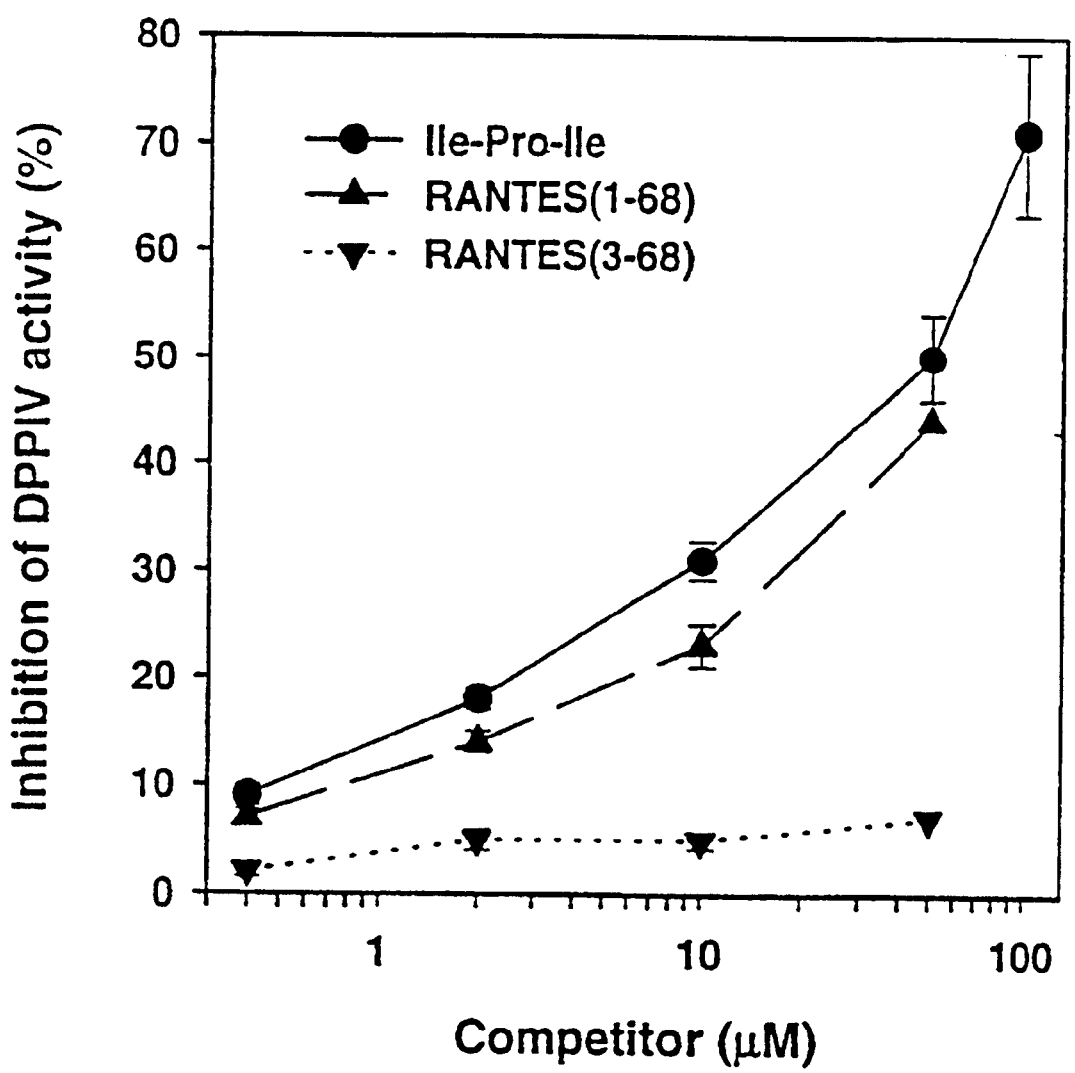
FIG. 2. Competitive inhibition of DPPIV by RANTES (1–68). Colorimetric DPPIV enzyme assay was performed using human placental DPPIV and the Gly-Pro-pNA substrate, in the presence or absence of the test competitors Ile-Pro-Ile, RANTES(1–68), or RANTES(3–68); the competitor concentration is indicated on the horizontal axis. Data are means±SEM (n=3), except for the highest concentration of RANTES(1–68) and RANTES(3–68), for which only one sample was assayed in order to conserve material. Similar results were obtained in a repeat experiment.

ES-MS analysis revealed that 100 nM rhRANTES underwent partial to complete hydrolysis when incubated overnight at 37° C. with increasing amounts (25 to 250 (U) of sCD26 (FIG. 1). Taking into account cationization (K+) of the multiply charged ions, the measured molecular masses of the native and degraded polypeptides corresponded to the theoretical masses of full-length (residues 1 to 68) and truncated (residues 3 to 68) forms of RANTES, respectively. The calculated difference between the molecular masses of the native and the truncated forms ranged from 183 to 185 daltons, which is consistent with the expected mass (184 daltons) of a released Ser-Pro dipeptide, the predicted NH2-terminus of RANTES (16). In contrast to the effect of enzymatically active sCD26, shortened RANTES was not generated by incubation of the chemokine with a mutant sCD26 deficient in enzyme activity (FIG. 1). RANTES also inhibited, possibly in a competitive manner, the rapid hydrolysis of a pNA-conjugated Gly-Pro dipeptide by human placental DPPIV, as measured in a colorimetric enzyme assay (FIG. 2). The efficacy of inhibition by chemically synthesized RANTES(1–68) was similar to that observed with the DPPIV substrate and competitive inhibitor Ile-Pro-Ile (Diprotin A) (17), whereas RANTES (3–68) did not inhibit the reaction.

EXAMPLE 3

Sensitivity to CD26-mediated Cleavage

Sensitivity to CD26-mediated cleavage was not a unique property of RANTES (Table 1.). Cleavage products with the predicted molecular masses were also evident in samples of MCP-2, eotaxin and IP-10 after incubation with sCD26. In contrast, MCP-1, which has a 62% sequence similarity with MCP-2 including the NH2-terminal QP dipeptides, was not cleaved by the enzyme under the same experimental conditions.

EXAMPLE 4

CD26-specific Truncation of RANTES Modifies Its Target Cell Specificity

Figure 3:
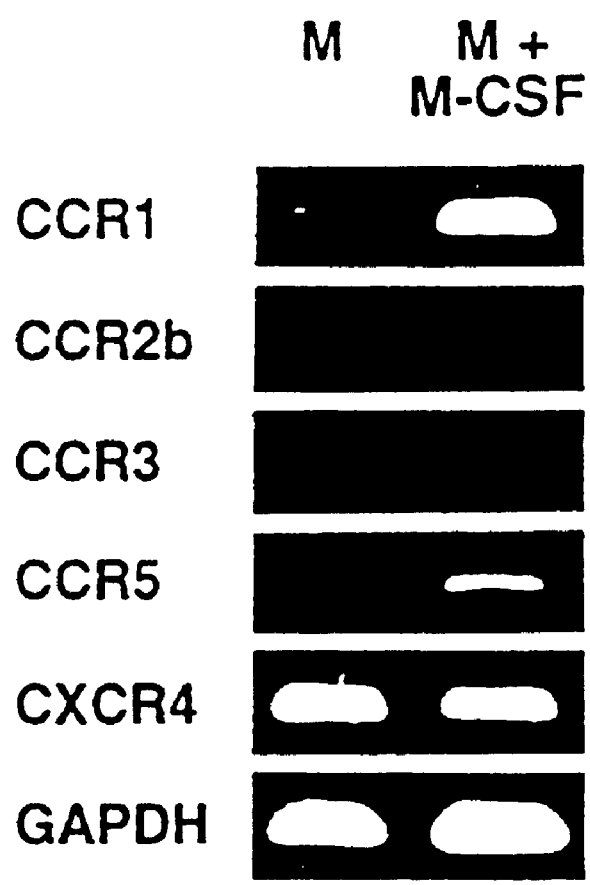
FIG. 3. RT-PCR analysis of chemokine receptor transcripts in monocytes cultured in the absence (M) or presence (M+M-CSF) of M-CSF. Total cellular RNA was subjected to RT-PCR analysis as described in Materials and Methods. Control reactions performed without reverse transcriptase were negative for each PCR product.

To investigate the functional significance of DPPIV-mediated truncation of RANTES, we compared the effects of chemically synthesized RANTES(1–68) and RANTES (3–68) on monocytes and monocyte-derived macrophages. Both resting cells and cells activated with M-CSF were analyzed because RT-PCR revealed marked changes in the abundance of chemokine receptor transcripts in response to M-CSF activation (FIG. 3). In resting cells, transcripts encoding the chemokine receptors CCR1, CCR2b, or CXCR4, as well as control glyceraldehyde phosphate dehydrogenase (GAPDH) mRNA, were readily detectable, whereas CCR5 receptor transcripts were virtually absent. After differentiation to macrophages, the intensity of the CXCR4 and GAPDH signals remained virtually unchanged, whereas the abundance of CCR1 and CCR5 mRNAs increased substantially and the CCR2b transcript virtually disappeared. CCR3 mRNA was not detected in either cell type.

Figure 4:
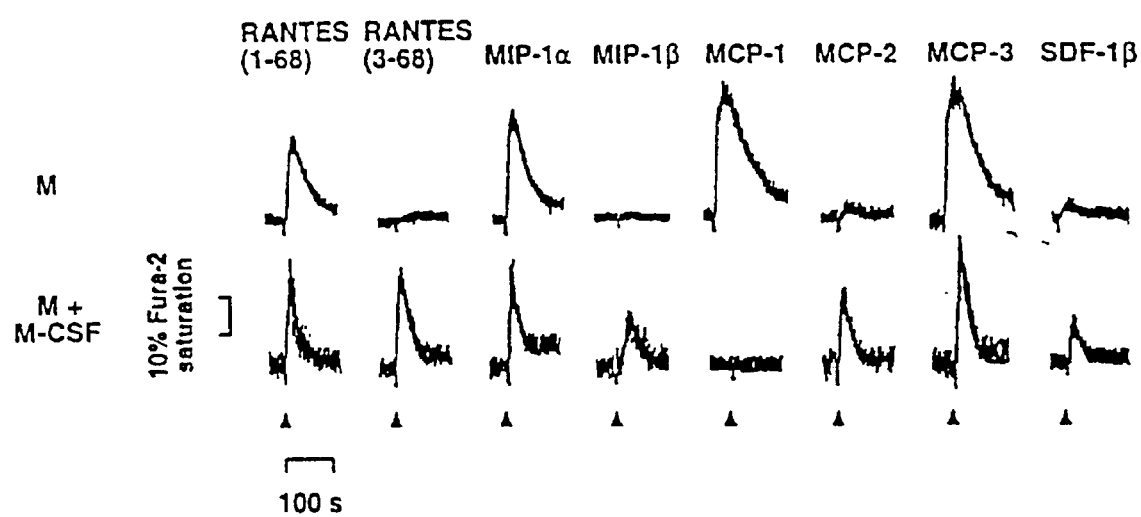
FIG. 4. Effects of chemokines on [Ca2+]i in monocytes cultured in the absence (M) or presence (M+M-CSF) of M-CSF. Fura-2 labeled cells were exposed (at the times indicated by arrowheads) to chemically synthesized RANTES variants (100 nM) or other indicated rh chemokines (30 nM) (R & D Systems), and Ca2+ responses were measured. The final concentrations of chemokines in this and subsequent experiments were sufficient to induce a maximal increase in [Ca2+]i in the responding cells, and further challenge with the same dose produced little or no detectable change in [Ca2+]i. The duration (~100 s) and amplitude (~20 to 30% of Fura-2 saturation) of Ca2+ responses were similar to those obtained for chemokines with human monocytes (36). Similar results were obtained in two additional experiments.

Transient changes in the cytosolic free Ca2+ concentration ([Ca2+]i) were recorded after stimulation of monocytes or macrophages with an optimal concentration of RANTES (1–68) or RANTES(3–68), and the effects were compared with those of other chemokines (FIG. 4). Addition of 100 nM RANTES(1–68) to cells loaded with the fluorescent Ca2+ probe Fura-2 induced a rapid increase in [Ca+]i in both monocytes and macrophages. In contrast, the same concentration of RANTES(3–68) increased [Ca2+]i in macrophages but not in monocytes. Among the other chemokines tested, macrophage inflammatory protein-1((MIP-1( ), monocyte chemotactic protein-1( ) (MCP-1), MCP-3 (1, 6), and stromal-derived factor-1((SDF-10 (18–20) also increased [Ca2+]i in resting monocytes, whereas MCP-2 (21) induced a barely detectable response and MIP-1((1, 6) was inactive. On the basis of the previously described receptor specificities of these chemokines (1, 6, 19, 20), the obtained activity pattern is consistent with expression of CCR1, CCR2b, and CXCR4 receptors on monocytes (FIG. 3). Macrophages showed marked Ca2+ responses to MIP-1(, MIP-1(, MCP-2, MCP-3, and SDF-1(, but were resistant to MCP-1, consistent with the presence of transcripts encoding CCR1, CCR5, and CXCR4, and the absence of those encoding CCR2b, in these cells (FIG. 3).

EXAMPLE 5

RANTES(3–68) Is a Chemokine Agonist, with Altered Receptor Specificity

Figure 5:
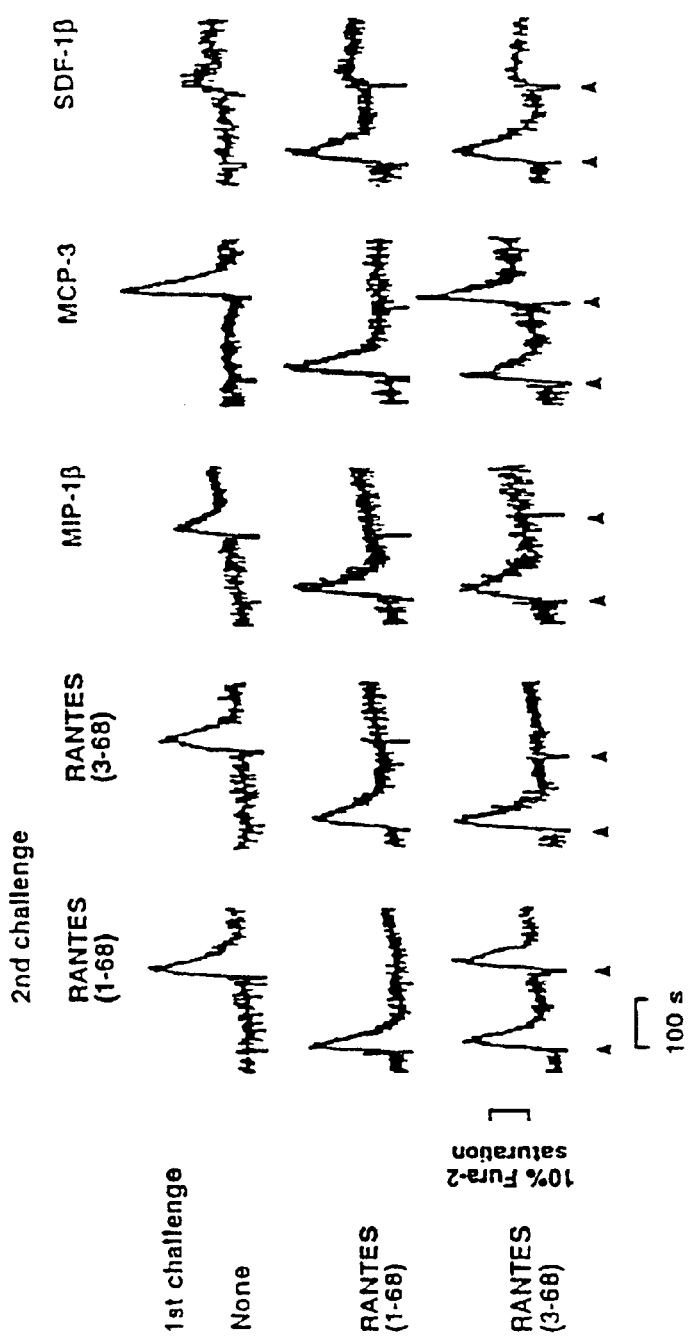
FIG. 5. Desensitization of chemokine-induced Ca2+ responses by full-length or truncated RANTES. Fura-2 labeled cells were stimulated first with 100 nM RANTES (1–68) or RANTES(3–68), or were left unstimulated. After ~150 s, the cells were challenged with the RANTES variants (100 nM) or other chemokines (30 nM) as indicated, and Ca2+ responses were measured.

Agonists that act at common chemokine receptors block each other's activity as a result of receptor desensitization, whereas responses to chemokines that act at different receptors are generally not affected (1, 6). We therefore performed comparative desensitization experiments to define the types of receptors that mediate the effects of native versus truncated RANTES in macrophages (FIG. 5). Macrophages that were stimulated first with 100 nM RANTES(1–68) did not exhibit a second Ca2+ response when challenged with the same dose of either full-length or truncated RANTES. In contrast, cells stimulated with 100 nM RANTES(3–68) fully retained their ability to respond to a subsequent challenge with full-length RANTES, but were desensitized to the effect of the truncated form. These results suggest that the receptor repertoire available for truncated RANTES is more restricted than that available for the native chemokine. To characterize further the receptor usage of the different forms of RANTES and other chemokines, we also studied the sensitivity of MIP-1(-, MCP-3-, and SDF-1(-induced Ca2+ responses to RANTES-mediated receptor desensitization (FIG. 5). Of the known receptors, RANTES signals via CCR1, CCR4, and CCR5, whereas MIP-1(acts at CCR5 exclusively and MCP-3 binds only to CCR1 and CCR2b at the concentrations used in our experiments (1, 6). The only receptor known to bind SDF-1(is CXCR4 (19, 20). Pretreatment of macrophages with full-length RANTES blocked the ability of MIP-1(and MCP-3, but not that of SDF-1(, to increase [Ca2+]i. In contrast, RANTES(3–68) desensitized cells to the effect of MIP-1(but did not affect the response to MCP-3 or SDF-1. These results are consistent with previous data on RANTES-induced receptor desensitization (1) and with our data on chemokine receptor mRNA abundance (FIG. 3). They suggest that, in M-CSF-activated macrophages, full-length RANTES shares CCR1 and CCRS receptors with MCP-3 and MIP-1(, respectively. Our results also indicate that, without its two NH2-terminal residues, RANTES is still able to signal via CCR5 but can no longer act at the CCR1 receptor.

EXAMPLE 6

CCR1- and CCR5-mediated Signaling of RANTES

Figure 6:
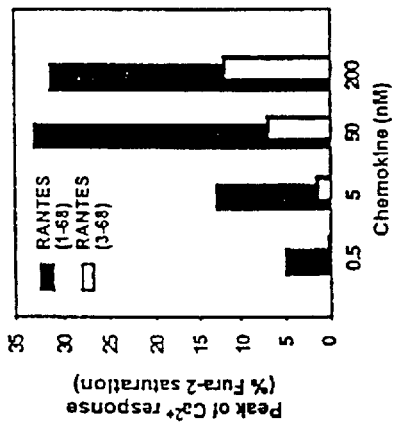
FIG. 6. Activity of flull-length and truncated RANTES in cells expressing recombinant CCR5 or CCR1 receptors. The [Ca2+]i was measured in HEK-293 cells expressing CCR5 (A and C) and HOS-CD4 cells expressing CCR1 (B and D). (A and B) Cells were stimulated with various concentrations of the two RANTES variants as indicated and maximal fluorescence values were calculated from the peaks of the Ca2+ response curves. (C and D) Homologous and heterologous desensitization of the responses induced by RANTES(1–68) and RANTES(3–68) was measured in transfectants as described in FIG. 5.
Figure 6:
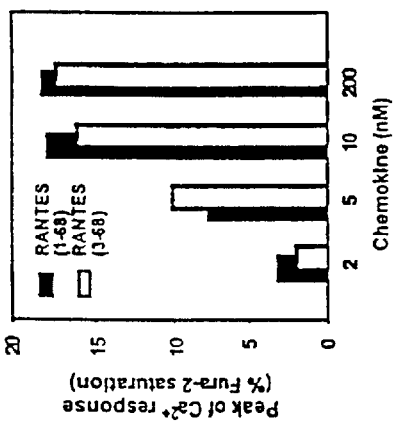
Figure 6:
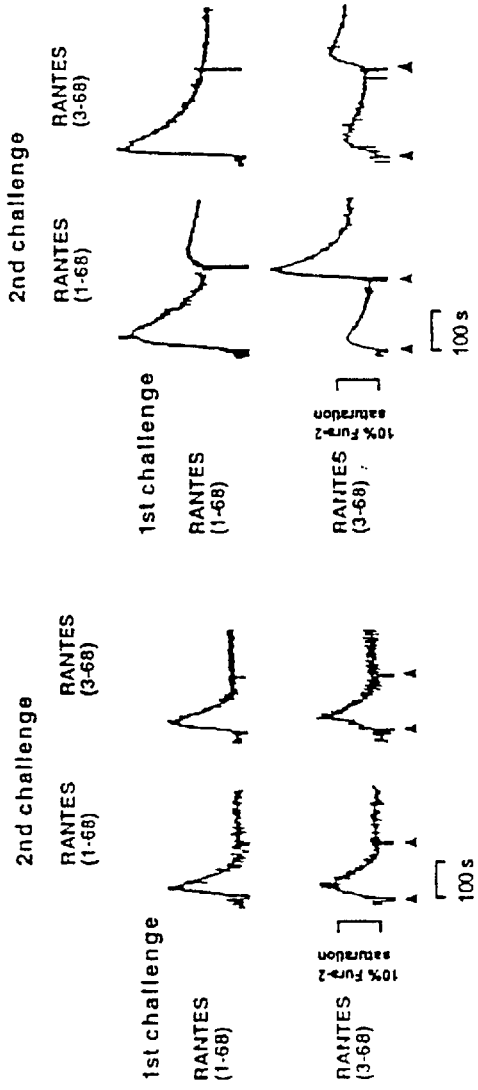

HEK-293 cells expressing CCR5 and HOS-CD4 cells expressing CCR1 were loaded with Fura-2 and exposed to various concentrations of RANTES(1–68) or RANTES (3–68). The two RANTES variants showed similar abilities to increase [Ca2+]i in the CCR5 transfectant (FIG. 6A); the responses were dose dependent, with 10 nM of each variant sufficient to induce a maximal Ca2+ response. In contrast, in the cells expressing CCR1, the amount of RANTES(3–68) required to produce a detectable Ca2+ response was ~100 times that for RANTES (1–68) (FIG. 6B); the effect of RANTES(1–68) saturated at 50 nM, whereas that of RANTES(3–68) appeared not to have achieved saturation at 200 nM. Furthermore, bidirectional cross-desensitization between the two RANTES variants was evident only with the cells expressing CCR5 (FIG. 6C); in the CCR1 transfectant, cross-desensitization was induced by full-length RANTES but not by the truncated form, which also did not exhibit self-desensitization (FIG. 6D). Control cells transfected with vector alone or with vectors encoding CCR2b, CCR3, or CXCR4 did not respond to these ligands (data not shown). These results thus confirm that the native and CD26-truncated RANTES variants exhibit markedly different activities at the CCR1 receptor.

EXAMPLE 7

RANTES(3–68) Is a Potent Inhibitor of HIV-1

Figure 7:
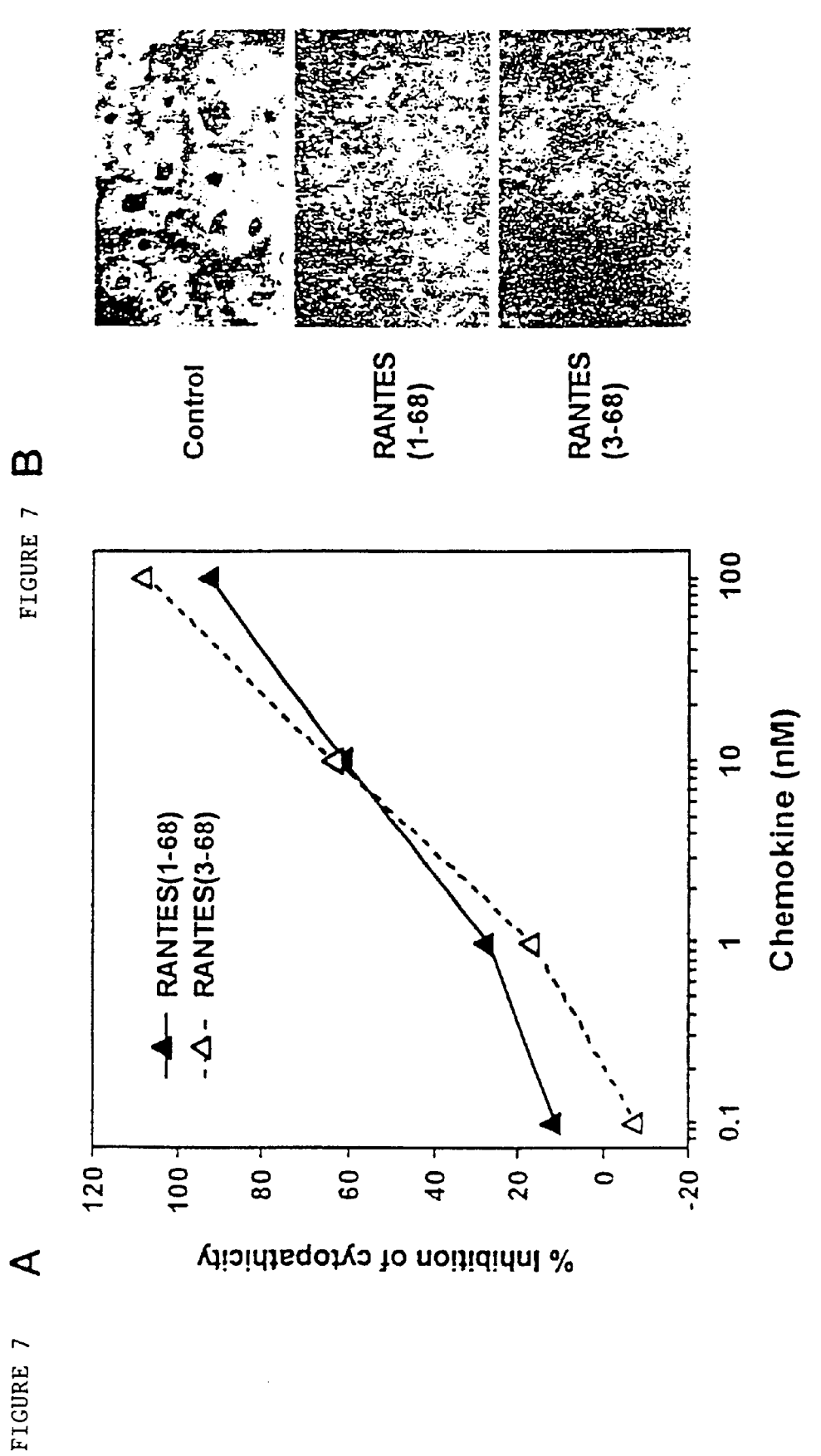
FIG. 7. Effects of full-length and truncated RANTES on HIV-1-induced cytopathicity. (A) HOS-CD4.CCR5 cells were incubated with uninfected PM1 cells or PM1 cells chronically infected with MV3-HXB2 virus in the presence or absence of the indicated concentrations of RANTES variants. After 3 days, cell viability was measured by the XTT method. Data are means of triplicate samples (SEM, <20% of mean). (B) Representative photomicrographs of HOS-CD4.CCR5 cells cultured with HIV-1-infected PM1 cells in the absence or presence of RANTES (1–68) or RANTES(3–68) as indicated.

In addition to their function in chemotaxis, RANTES, MIP-1(, and MIP-1(each inhibit HIV-1 infection by competitive binding to CCR5 (22–27), and this inhibition does not require receptor-mediated cell signaling (27, 28). To examine whether removal of the two NH2-terminal residues affects the antiviral activity of RANTES, we mixed HOS-CD4 cells expressing recombinant CCR5 and PM1 cells chronically infected with the M-tropic recombinant MV3-HXB2 virus and cocultured them in the absence or presence of various concentrations of RANTES(1–68) or RANTES (3–68). Both RANTES variants inhibited HIV-1-induced syncytium formation and cytopathicity (FIG. 7). Thus, similar to signaling activity through CCR5, competitive inhibition of HIV-1 infection does not require the NH2-terminal Ser-Pro residues of RANTES.

The CD26 cleavage product of RANTES, RANTES (3–68), acts as a chemokine agonist with altered receptor-specificity. Hydrolysis by CD26 might explain why RANTES(3–68) has been isolated as a second component in addition to intact RANTES from culture supernatants of stimulated human fibroblasts, skin samples, and platelet preparations (29, 30). The CC-chemokines RANTES, MCP-2, and eotaxin, and the CXC-chemokine IP-10 are the first immune modulators and the longest polypeptides identified as natural substrates for CD26.

CD26 exists in both soluble and membrane-expressed forms. Secreted forms of CD26 have been identified in cell cultures and in human serum (31, 32), although CD26 may be more active when expressed as an ectoenzyme at high concentrations on endothelial cells, hepatocytes, kidney brush border membranes, and leukocytes (10). Up-regulation of CD26 expression on T lymphocytes and macrophages has been linked to cell activation and development of immunological memory (10). Thus, activation-induced changes in CD26 expression could affect the course of an inflammatory response by modifying the target cell specificity of RANTES or other chemokines, and by regulating the equilibrium between the migrating cell subsets. We are currently addressing whether cells with different levels of CD26 expression (e.g. naive versus memory T cells) secrete truncated forms of RANTES or other chemoattractants, or are capable of modifying exogenous chemokines.

The differential effects of CD26-truncated RANTES on monocytes versus macrophages illustrate a role for cell differentiation in regulating chemokine sensitivity through altered receptor expression. Our functional and receptor transcript data indicate that CCR1 and CCR2b may be the two principal CC chemokine receptors in resting monocytes, although other unidentified and functionally overlapping receptors may also contribute to chemokine function. Cell differentiation markedly changes the pattern of chemokine sensitivity by reducing CCR2b expression, thereby rendering the cells resistant to MCP-1, while increasing CCR5 expression, thereby augmenting the responses to CD26-truncated RANTES and MIP-1(. An increase in CCR5 expression also may render macrophages more susceptible to infection by M-tropic variants of HIV-1. We have shown that macrophages also express CXCR4, the coreceptor for T cell line-tropic HIV-1 variants (33–34), as assessed by receptor transcript abundance and functional activity of the CXCR4 ligand SDF-1(. Nevertheless, activated macrophages are relatively resistant to infection by T cell line-tropic HIV-1 variants (35), which suggests that factors other than CXCR4 may also be required for efficient infection of macrophages by these types of viruses.

Removal of two NH2-terminal residues by CD26 abolishes the interaction of RANTES with CCR1, but does not affect the anti-HIV-1 activity or the CCR5 signaling properties of the chemokine. Proline residues also influence the susceptibility of proximal peptide bonds to proteolytic enzymes (6), and so the removal of such residues by CD26 may also reduce the half-life of RANTES and other chemokines during an inflammatory response. It will be important to determine whether CD26-mediated cleavage is a general mechanism for changing the receptor specificity and functional activity of other chemokines, including those examined in this study (MCP-2, eotaxin, and IP-10).

Many, but not all CC- and CXC-chemokines contain X-Pro- or X-Ala-amino-terminal sequence and are potential substrates of DPPIV. We are currently exploring whether the inability of CD26 to cleave MCP-1 is due to aggregation of this chemokine under these experimental conditions or to a conformational requirement of the enzyme that is not fulfilled by MCP-1. Selectivity of CD26 activity on chemokines may function to reduce redundancy in chemokine target cell specificity as illustrated by the different activity of full-length and truncated RANTES on monocytes versus macrophages. Finally, truncated analogs of chemokines with selective activity on distinct functional receptors, or analogs that resist CD26 cleavage, may prove therapeutically beneficial in blocking or inducing the infiltration of specific subsets of effector cells mediating inflammation, allergy and anti-tumor responses.

TABLE 1

Chemokine cleavage products after digestion with sCD26.

| Chemokine | NH2-terminal dipeptide | CD26 cleavage | Molecular masses by mass spectrometry (Da) | | | |
|---|---|---|---|---|---|---|
| | | | Full length | | Truncated | |
| | | | Theoretical | Observed | Theoretical | Observed |
| Eotaxin | GP | Yes | 8361 | 8361 | 8207 | 8207 |
| IP-10 | VP | Yes | 8633 | 8637/8751* | 8437 | 8440/8555* |
| MCP-1 | QP | No | 8681 | 8678 | 8456 | ND‖ |
| MCP-2 | QP | Yes | 8910 | 8909 | 8685 | 8686/8703# |

*Tentatively identified as [M + trifluoroacetic acid (TFA)]+; molecular mass of TFA is 114 Da.
Tentatively identified as [M + H2O]+.
‖ND = not detected.

REFERENCES

1. Murphy, P. M. 1996. Chemokine receptors: structure, function and role in microbial pathogenesis. Cytokine Growth Factor Rev. 7:47–64.
2. Sica, A., A. Saccani, A. Borsatti, C. A. Power, T. N. Wells, W. Luini, N. Polentarutti, S. Sozzani, and A. Mantovani. 1997. Bacterial lipopolysaccharide rapidly inhibits expression of C-C chemokine receptors in human monocytes. J. Exp. Med. 185:969–974
3. Weber, M., M. Uguccioni, M. Baggiolini, I. Clark-Lewis, and C. A. Dahinden. 1996. Deletion of the NH2-terminal residue converts monocyte chemotactic protein 1 from an activator of basophil mediator release to an eosinophil chemoattractant. J. Exp. Med. 183:681–685.
4. Gong, J.-H., M. Uguccioni, B. Dewald, M. Baggiolini, and I. Clark-Lewis. 1996. RANTES and MCP-3 antagonists bind multiple chemokine receptors. J. Biol. Chem. 271:10521–10527.
5. Arenzana-Seisdedos, F., J.-L. Virelizier, D. Rousset, I. Clark-Lewis, P. Loetscher, B. Moser, and M. Baggiolini. HIV blocked by chemokine antagonist. 1996. Nature. 383:400.
6. Murphy, P. M. 1994. The molecular biology of leukocyte chemoattractant receptors. Annu. Rev. Immunol. 12:593–633.
7. Walter, R., W. H. Simmons, and T. Yoshimoto. 1980. Proline specific endo- and exopeptidases. Mol. Cell. Biochem. 30:111–127.
8. Fox, D. A., R. E. Hussey, K. A. Fitzgerald, 0. Acuto, C. Poole, L. Palley, J. F. Daley, S. F. Schlossman, and E. L. Reinherz. 1984. Ta1, a novel 105 kD human T cell activation antigen defined by a monoclonal antibody. J. Immunol. 133:1250–1256.
9. Hegen, M., G. Niedobitek, C. E. Klein, H. Stein, and B. Fleischer. 1990. The T cell triggering molecule Tp103 is associated with dipeptidyl aminopeptidase IV activity. J. Immunol., 144:2908–2914.
10. Fleischer, B. 1994. CD26: a surface protease involved in T-cell activation. Immunol. Today. 15:180–184.
11. Oravecz, T., G. Roderiquez, J. Koffi, J. Wang, M. Ditto, D. C. Bou-Habib, P. Lusso, and M. A. Norcross. 1995. CD26 expression correlates with entry, replication and cytopathicity of monocytotropic HIV-1 strains in a T-cell line. Nature Med. 1:919–926.
12. Samson, M., O. Labbe, C. Mollereau, G. Vassart, and M. Parmentier. 1996. Molecular cloning and functional expression of a new human CC-chemokine receptor gene. Biochemistry. 35:3362–3367.
13. Tanaka, T., D. Camerini, B. Seed, Y. Torimoto, N. H. Dang, J. Kameoka, H. N. Dahlberg, S. F. Schlossman, and C. Morimoto. 1992. Cloning and functional expression of the T cell activation antigen CD26. J Immunol. 149:481–486.
14. Davis, S. J., H. A. Ward, M. J. Puklavec, A. C. Willis, A. F. Williams, and A. N. Barclay. 1990. High level expression in Chinese hamster ovary cells of soluble forms of CD4 T lymphocyte glycoprotein including glycosylation variants. J. Biol. Chem. 265:10410–10418.
15. McCaughan, G. W, J. E. Wickson, P. F. Creswick, and M. D. Gorrell. 1990. Identification of the bile canalicular cell surface molecule GP110 as the ectopeptidase dipeptidyl peptidase IV: an analysis by tissue distribution, purification and N-terminal amino acid sequence. Hepatology. 11:534–544.
16. Schall, T. J., J. Jongstra, B. J. Dyer, J. Jorgensen, C. Clayberger, M. M. Davis, and A. M. Krensky. 1988. A human T cell-specific molecule is a member of a new gene family. J. Immunol. 141:1018–1025.
17. Rahfeld, J., M. Schierhorn, B. Hartrodt, K. Neubert, and J. Heins. 1991. Are diprotin A (Ile-Pro-Ile) and diprotin B (Val-Pro-Leu) inhibitors or substrates of dipeptidyl peptidase IV? Biochim. Biophys. Acta. 1076:314–316.
18. Nagasawa, T., H. Kikutani, and T. Kishimoto. 1994. Molecular cloning and structure of a pre-B-cell growth-stimulating factor. Proc. Natl. Acad. Sci. U.S.A. 91:2305–2309.
19. Bleul, C. C., M. Farzan, H. Choe, C. Parolin, I. Clark-Lewis, J. Sodroski, and T. A. Springer. 1996. The lymphocyte chemoattractant SDF-1 is a ligand for LESTR/fusin and blocks HIV-1 entry. Nature. 382:829–833.
20. Oberlin, E., A. Amara, F. Bachelerie, C. Bessia, J.-L. Virelizier, F. Arenzana-Seisdedos, O. Schwartz, J.-M. Heard, I. Clark-Lewis, D. F. Legler, M. Loetscher, M. Baggiolini, and B. Moser. 1996. The CXC chemokine SDF-1 is the ligand for LESTR/fusin and prevents infection by T-cell-line-adapted HIV-1. Nature. 382:833–835.
21. Van Damme, J., P. Proost, J.-P. Lenaerts, and G. Opdenakker. 1992. Structural and functional identification of two human, tumor-derived monocyte chemotactic proteins (MCP-2 and MCP-3) belonging to the chemokine family. J. Exp. Med. 176:59–65.

22. Alkathib, G., C. Combadiere, C. C. Broder, Y. Feng, P. E. Kennedy, P. M. Murphy, and E. A. Berger. 1996. CC CKR5: A RANTES, MIP-1(, MIP-1(, receptor as a fusion cofactor for macrophage-tropic HIV-1. Science. 272:1955–1958.
23. Choe, H., M. Farzan, Y. Sun, N. Sullivan, B. Rollins, P. D. Ponath, L. Wu, C. R. Mackay, G. LaRosa, W. Newman, N. Gerard, C. Gerard, and J. Sodroski. 1996. The (-chemokine receptors CCR3 and CCR5 facilitate infection by primary HIV-1 isolates. Cell. 85:1135–1148.
24. Doranz, B. J., J. Rucker, Y. Yi, R. J. Smyth, M. Samson, S. C. Peiper, M. Parmentier, R. G. Collman, and R. W. Doms. 1996. A dual-tropic primary HIV-1 isolate that uses fusin and the (-chemokine receptors CKR-5, CKR-3, and CKR-2b as fusion cofactors. Cell. 85:1149–1158.
25. Deng, H., R. Liu, W. Ellmeier, S. Choe, D. Unutmaz, M. Burkhart, P. Di Marzio, S. Marmon, R. E. Sutton, C. M. Hill, C. B. Davis, S. C. Peiper, T. J. Schall, D. R. Littman, and N. R. Landau. 1996. Identification of a major co-receptor for primary isolates of HIV-1. Nature. 381:661–673.
26. Dragic, T., V. Litwin, G. P. Allaway, S. R. Martin, Y. Huang, K. A. Nagashima, C. Cayanan, P. J. Maddon, R. A. Koup, J. P. Moore, and W. A. Paxton. 1996. HIV-1 entry into CD4+ cells is mediated by the chemokine receptor CC-CKR-5. Nature 381:667–673.
27. Oravecz, T., M. Pall, and M. A. Norcross. 1996. (-chemoldne inhibition of monocytotropic HIV-1 infection: Interference with a postbinding fusion step. J. Immunol. 157:1329–1332.
28. Farzan, M., H. Choe, K. A. Martin, Y. Sun, M. Sidelko, C. R. Mackay, N. P. Gerard, J. Sodroski, and C. Gerard. 1997. HIV-1 entry and macrophage inflammatory protein-1beta-mediated signaling are independent functions of the chemokine receptor CCR5. J. Biol. Chem. 272:6854–6857.
29. Mallet, A. I., and I. Kay. 1995. Characterization of chemokine proinflammatory proteins by combined liquid chromatography-mass spectrometry. Biochem. Soc. Trans. 23:911–913.
30. Noso, N. M., Sticherling, J. Bartels, A. I. Mallet, E. Christophers, and J.-M. Schr+der. 1996. Identification of an N-terminally truncated form of the chemokine RANTES and granulocyte-macrophage colony-stimulating factor as major eosinophil attractants released by cytokine-stimulated dermal fibroblasts. J. Immunol. 156:1946–1953.
31. Tanaka, T., J. S. Duke-Cohan, J. Kameoka, A. Yaron, I. Lee, E. F. Schlossman, and C. Morimoto. 1994. Enhancement of antigen-induced T-cell proliferation by soluble CD26/dipeptidyl peptidase IV. Proc. Natl. Acad. Sci. U.S.A. 91:3082–3086.
32. Duke-Cohan, J. S., C. Morimoto, J. A. Rocker, and S. Schlossman. 1996. Serum high molecular weight dipeptidyl peptidase IV (CD26) is similar to a novel antigen DPPT-L released from activated T cells. J. Immunol. 156:1714–1721.
33. Feng, Y., C. C. Broder, P. E. Kennedy, and E. A. Berger. 1996. HIV-1 entry cofactor: Functional cDNA cloning of a seven-transmembrane, G protein-coupled receptor. Science. 272:872–876.
34. Berson, J. F., D. Long, B. J. Doranz, J. Rucker, F. R. Jirik, and R. W. Doms. 1996. A seven-transmembrane domain receptor involved in fusion and entry of T-cell-tropic human immunodeficiency virus type 1 strains. J. Virol. 70:6288–6295.
35. Cheng-Mayer, C., M. Quiroga, J. W. Tung, D. Dina, and J. A. Levy. 1990. Viral determinants of human immunodeficiency virus type 1 T-cell or macrophage tropism, cytopathogenicity, and CD4 antigen modulation. J. Virol. 64:4390–4398.
36. Wang, J. M., D. W. McVicar, J. J. Oppenheim, and D. J. Kelvin. 1993. Identification of RANTES receptors on human monocytic cells: competition for binding and desensitization by homologous chemotactic cytokines. J. Exp. Med. 177:699–705.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

---

What is claimed is:

1. A substantially pure polypeptide having an amino acid sequence as set forth in SEQ ID NO:2 which is a truncated form of RANTES (1–68), said polypeptide comprising the amino acid sequence as set forth in SEQ ID NO:2.

2. An isolated polynucleotide which encodes an amino acid sequence as set forth in claim 1.

3. An isolated polynucleotide selected from the group consisting of
   a) SEQ ID NO:1;
   b) SEQ ID NO:1, wherein T can also be U;
   c) nucleic sequences fully complementary to SEQ ID NO:1;
   d) fragments of a), b), or c) that are at least 15 bases in length and that will hybridize to DNA which encodes SEQ ID NO:2.

4. An expression vector containing in operable linkage the polynucleotide as in claim 2.

5. A host cell containing the vector of claim 4.

6. The host cell of claim 5, wherein the cell is a eukaryotic cell.

7. A substantially pure polypeptide consisting of the amino acid sequence as set forth in SEQ ID NO:2.

* * * * *